US00PP24741P3

(12) United States Plant Patent
Sproul

(10) Patent No.: US PP24,741 P3
(45) Date of Patent: Aug. 12, 2014

(54) SHRUB ROSE PLANT NAMED 'SPROPOM'

(50) Latin Name: *Rosa hybrida*
Varietal Denomination: Spropom

(71) Applicant: CP Delaware, Inc., Wilmington, DE (US)

(72) Inventor: James A. Sproul, Bakersfield, CA (US)

(73) Assignee: CP Delaware, Inc., Wilmington, DE (US)

( * ) Notice: Subject to any disclaimer, the term of this patent is extended or adjusted under 35 U.S.C. 154(b) by 58 days.

(21) Appl. No.: 13/573,826

(22) Filed: Oct. 9, 2012

(65) Prior Publication Data

US 2014/0101795 P1 Apr. 10, 2014

(51) Int. Cl.
*A01H 5/00* (2006.01)

(52) U.S. Cl.
USPC ..... Plt./102

(58) Field of Classification Search
USPC ..... Plt./102, 107, 108
See application file for complete search history.

(56) References Cited

U.S. PATENT DOCUMENTS

PP7,215 P * 4/1990 Austin ..... Plt./106
PP23,580 P3 * 5/2013 Sproul ..... Plt./104

* cited by examiner

*Primary Examiner* — Wendy C Haas
(74) *Attorney, Agent, or Firm* — Buchanan, Ingersoll & Rooney PC

(57) ABSTRACT

A new and distinct variety of shrub rose plant is provided which forms in abundance on a substantially continuous basis attractive semi-double blossoms that are reddish-purple with red coloration toward the center of the petals. The blossom size is large for the size of the plant. The vegetation is vigorous and strong and the growth habit is upright and bushy. Attractive ornamental glossy medium green foliage is formed. The plant is particularly well suited for growing in a Western landscape. Distinctive ornamentation is provided.

1 Drawing Sheet

Botanical/commercial classification: *Rosa hybrida*/Shrub Rose Plant.

Varietal denomination: cv. Spropom.

SUMMARY OF THE INVENTION

The new variety of landscape shrub rose plant of the present invention was created by artificial pollination carried out in April/May 2008 at Bakersfield, Calif., U.S.A., wherein two parents were crossed which previously had been studied in the hope that they would contribute the desired characteristics. Each parent possessed a complex parentage as indicated hereafter. More specifically, the parentage of the female parent (i.e., seed parent) can be summarized as follows: <{'MORtoday'×['Geisha'×('KINbo'×'Macivy')]}×('WEKblusi'×'SCRivluv')>×mixed Hulthemia pollen. The parentage of the male parent (i.e., pollen parent) can be summarized as follows: <{[('Orangeade'×'Auscot')×'WEKfabpur']×mixed pollen}×mixed Hulthemia pollen>×mixed Hulthemia pollen. The 'WEKblusi' variety is the subject of U.S. Plant Pat. No. 10,188, and the 'Auscot' variety is the subject of U.S. Plant Pat. No. 7,215. The other ancestoral plants identified herein as well as the seed and pollen parents are non-patented in the United States.

The seeds resulting from the above pollination were sown and small plants were obtained which were physically and biologically different from each other. Selective study resulted in the identification of a single plant of the new variety.

It was found that the new variety of landscape shrub rose plant of the present invention possesses the following combination of characteristics:

(a) abundantly and substantially continuously forms attractive large semi-double blossoms that are reddish-purple with red coloration toward the center of the blossoms,
(b) exhibits an upright and bushy growth habit,
(c) forms vigorous and strong vegetation,
(d) forms attractive ornamental medium green foliage with a glossy finish, and
(e) is well suited for providing distinctive ornamentation.

A new rose variety is provided having attractive multicolored blossoms, combined with substantially continuous blooming. The plant reblooms well and displays an attractive bushy growth habit. The flowers are large for the plant size.

The new variety well meets the needs of the horticultural industry particularly when grown in the Western landscape. It can be grown to advantage as attractive ornamentation in parks, gardens, public areas, and residential landscapes. The lavender and red blossom coloration contrasts nicely with the medium green foliage.

The new variety can be readily distinguished from its parental plants. More specifically, the female parent displays an even more upright growth habit, even more glossy foliage, and forms orange blossoms with a smaller central blotch. The male parent displays a dissimilar compact growth habit and forms cream-colored blossoms with a larger central blotch.

The new variety also can be readily distinguished from the 'Sprolem' variety (U.S. Plant Pat. No. 23,580), as well as other plants in its ancestry. More specifically, the 'Sprolem' variety displays a considerably larger growth habit and forms bright yellow blossoms. The 'MORtoday' variety displays pink blossoms with lavender at the base. The 'Geisha' variety displays mauve blossoms. The 'KINbo' variety forms double deep yellow blossoms. The 'Macivy' variety displays very double apricot blossoms. The 'WEKblusi' variety displays large double silvery gray lavender blossoms. The 'SCRivluv' variety displays single deep yellow blossoms. The 'Orangeade' variety displays orange to orange-red blossoms. The 'Auscot' variety forms very large very double pink/pale red blossoms with yellow at the base. The 'WEKfabpur' variety forms purple blossoms with a lighter under surface. It is recognized that Hulthemia roses generally bloom only once a year and generally display an unattractive growth habit.

The characteristics of the new variety have been found to be homogeneous and stable and are strictly transmissible by asexual propagation by the use of cuttings from one generation to another at Wasco, Calif., U.S.A. Accordingly, the new variety can be asexually reproduced in a true-to-type manner.

The new variety has been named 'Spropom', and will be marketed under the EYECONIC and POMEGRANATE LEMONADE trademarks.

BRIEF DESCRIPTION OF THE PHOTOGRAPH

The accompanying photograph shows, as nearly true as it is reasonably possible to make the same in a color illustration of this character, typical blossoms and foliage of the new variety. The illustrated plant was approximately two years of age and was growing outdoors on its own roots in the field at Wasco, Calif., U.S.A.

DETAILED DESCRIPTION

The chart used in the identification of colors is that of The Royal Horticultural Society (R.H.S. Colour Chart-1995 Edition or equivalent). The description is based on the observation of two-year-old specimens of the new variety during May while growing on their own roots in a greenhouse at West Grove, Pa., U.S.A.

Class: Shrub Rose.

Plant:

*Height*.—Approximately 12 inches when mature.

*Width*.—Approximately 18 inches when mature.

*Habit*.—Upright and bushy.

Branches:

*Color*.—Young stems: near Yellow-Green Group 144B. Adult wood: near Greyed-Orange Group 165A.

*Texture*.—Young stems: smooth. Adult wood: somewhat rough.

*Thorns*.—Size: approximately 2 to 5 mm in length on average. Quantity: moderate. Color on young stems: Greyed-Orange Group 166D. Color on mature wood: Greyed-Orange Group 165D.

Leaves:

*Size*.—A five-leaflet leaf commonly is approximately 7 cm in length on average, and approximately 4.8 cm in width on average.

*Leaflets*.—Number: 3, 5, and 7. Shape: broadly ovate with a serrate margin. Texture (upper surface): smooth and glossy. Texture (under surface): smooth. Size: terminal leaflets commonly are approximately 2.8 cm in length on average and approximately 2.1 cm in width on average, and lower leaflets commonly are approximately 1.8 cm in length on average and approximately 1.7 cm in width on average. Color (young foliage): Yellow-Green Group 144A edged with Red-Purple Group 59A on the upper surface, and Yellow-Green Group 144B edged with Red-Purple Group 59A on the under surface. Color (fully mature foliage): commonly near Green Group 137A on the upper surface, and Yellow-Green Group 147B on the under surface.

Inflorescence:

*Number of flowers*.—Singly or in cluster of up to approximately five blossoms per stem, and commonly approximately 10 flowers on plant at a given time.

*Peduncle*.—Smooth in texture, near Yellow-Green Group 144A in coloration, and approximately 4.5 cm in length on average.

*Sepals*.—Number: five. Length: commonly approximately 2 cm on average. Width: commonly approximately 6 mm on average. Upper surface: near Yellow-Green Group 146B, somewhat rough, and covered with short hairs. Under surface: smooth, and near Yellow-Green Group 144C and overlaid with Yellow-Green Group 144A in coloration.

*Buds*.—Shape: ovoid. Length: approximately 1.5 cm on average. Diameter: commonly approximately 1 cm on average. Color: near Red-Purple Group 60A when opening.

*Flower*.—Form: semi-double. Diameter: approximately 6.5 cm on average. Color (when opening begins): upper surface: near Red-Purple Group 61A at the point of attachment, transitioning to Red-Purple Group 67A, transitioning to Red-Purple Group 69A, and finally transitioning to Red-Purple Group 67A at the apex. undersurface: near White Group 155C at the point of attachment, and at the apex near Red-Purple Group 67B overlaid with White Group 155C. Color (when fully open): upper surface: near Red-Purple Group 71A at the point of attachment, transitioning to Red-Purple Group 58A, transitioning to White Group 155C, and finally transitioning to Red-Purple Group 67B overlaid with White Group 155C at the apex. under surface: near White Group 155A at the point of attachment, transitioning to Greyed-Purple Group 186C and White Group 155A at the apex. Color stability: the blossom coloration commonly tends to lighten throughout with full maturity. Fragrance: none noticeable. Petal shape: obcordate. Petal length: commonly approximately 2.8 cm on average. Petal width: commonly approximately 3.3 cm on average. Petal margin: entire. Petal apex: broadly obcordate. Petal base: broadly cuneate. Petal number approximately 10 on average. Lastingness: the blossoms commonly last approximately 5 days on the plant depending upon environmental conditions. Petal drop: good, with the petals commonly dropping cleanly and freely. Stamen number: approximately 77 on average. Anthers: near Yellow-Orange Group 17A in coloration. Filaments: near Yellow Group 14C at the top, transitioning to near Orange Group 26B, and finally transitioning to near Red Group 46A at the base. Pollen: near Yellow-Orange Group 17A in coloration. Pistils: separate and free, and commonly approximately 31 in number on average. Stigmas: near Yellow Group 4A in coloration, and approximately 1 mm in size. Styles: near Yellow Group 4C in coloration and approximately 8 mm in size. Receptacle: circular in shape, achenes stand on the bottom and wall, approximately 7 mm in diameter, and near Yellow-Green Group 144A in coloration.

Development:

*Vegetation*.—Vigorous and strong.

*Blossoming*.—Abundant and substantially continuous.

*Resistance to diseases*.—Typical for a shrub rose with some susceptibility to Black Spot. Accordingly, the plant is recommended for growing in the Western States.

*Propensity to form hips/seeds*.—Formed in a sparse quantity during observations to date.

*Hardiness*.—U.S.D.A. Hardiness Zone Nos. 6 to 9.

Plants of the new 'Spropom' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant characterized by the following combination of characteristics:

(a) abundantly and substantially continuously forms attractive large semi- double blossoms that are reddish-purple with red coloration toward the center of the blossoms, (b) exhibits an upright and bushy growth habit, (c) forms vigorous and strong vegetation, (d) forms attractive ornamental medium green foliage with a glossy finish, and (e) is well suited for providing distinctive ornamentation; substantially as herein shown and described.

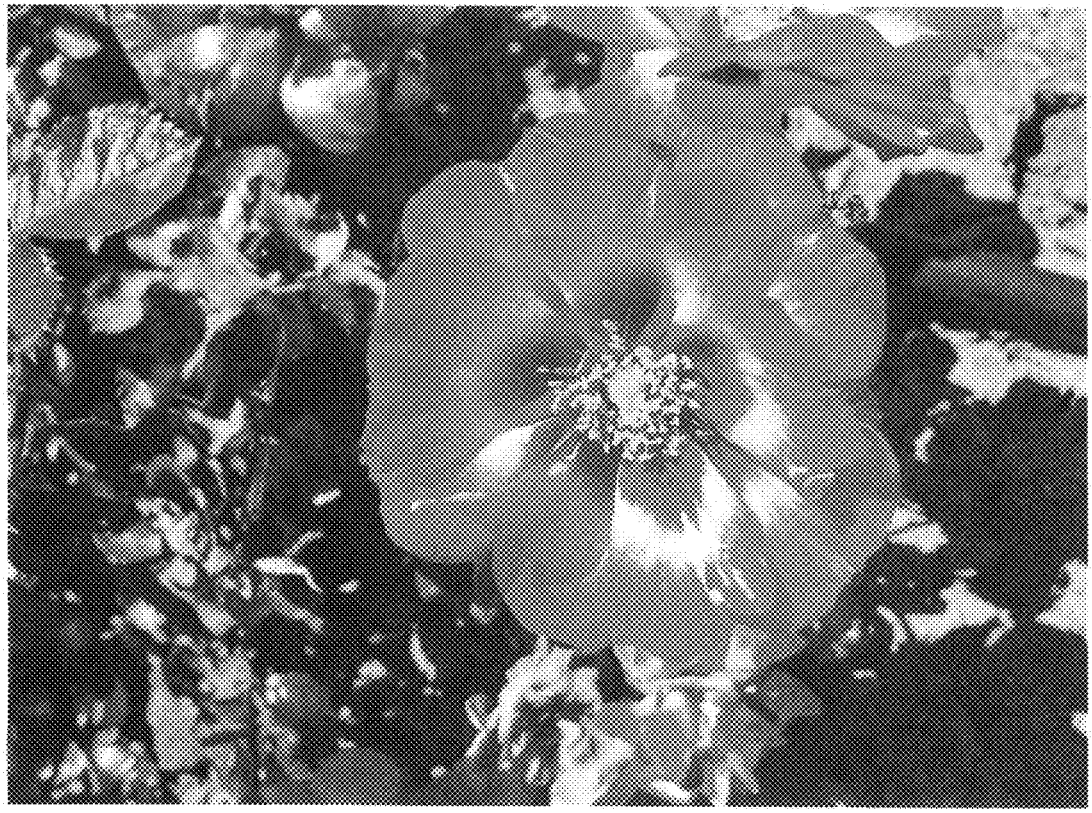

* * * * *